United States Patent
Curran et al.

(10) Patent No.: US 10,751,118 B2
(45) Date of Patent: Aug. 25, 2020

(54) MULTIPLE THERMOCOUPLE ASSEMBLY WITH REDUCED WIRE COUNT

(71) Applicant: St. Jude Medical, Cardiology Division, Inc., St. Paul, MN (US)

(72) Inventors: Timothy G. Curran, Ramsey, MN (US); Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 231 days.

(21) Appl. No.: 15/461,003

(22) Filed: Mar. 16, 2017

(65) Prior Publication Data

US 2017/0265931 A1   Sep. 21, 2017

Related U.S. Application Data

(60) Provisional application No. 62/311,284, filed on Mar. 21, 2016.

(51) Int. Cl.
    *A61B 18/14* (2006.01)
    *A61B 18/00* (2006.01)

(52) U.S. Cl.
    CPC ........ *A61B 18/148* (2013.01); *A61B 18/1492* (2013.01); *A61B 2018/00071* (2013.01); *A61B 2018/00089* (2013.01); *A61B 2018/00351* (2013.01); *A61B 2018/00577* (2013.01); *A61B 2018/00797* (2013.01); *A61B 2018/00821* (2013.01)

(58) Field of Classification Search
    CPC .......... A61B 2018/00577; A61B 2018/00791; A61B 2018/00797; A61B 2018/00821; A61B 18/148; A61B 18/1492
    See application file for complete search history.

(56) References Cited

U.S. PATENT DOCUMENTS

| | | | |
|---|---|---|---|
| 4,411,266 | A | 10/1983 | Cosman |
| 4,966,597 | A | 10/1990 | Cosman |
| 5,688,267 | A | 11/1997 | Panescu |
| 5,897,552 | A | 4/1999 | Edwards et al. |
| 6,045,550 | A | 4/2000 | Simpson et al. |
| 6,049,737 | A | 4/2000 | Simpson et al. |
| 6,582,425 | B2 | 6/2003 | Simpson |
| 6,616,657 | B2 | 9/2003 | Simpson et al. |

(Continued)

FOREIGN PATENT DOCUMENTS

| | | |
|---|---|---|
| CN | 104146761 A | 11/2014 |
| WO | 1996000036 A1 | 1/1996 |

(Continued)

*Primary Examiner* — Michael F Peffley
*Assistant Examiner* — Samantha M Good
(74) *Attorney, Agent, or Firm* — Dykema Gossett PLLC

(57) ABSTRACT

A multiple thermocouple assembly with a reduced wire count is configured for use in an ablation catheter tip. In at least one embodiment, the assembly comprises a first metal material comprising a plurality of junctions; a plurality of conductors comprising a second metal material, each conductor connected to the first metal material at one of the plurality of junctions; and a common conductor that is physically paired with at least one of the plurality of conductors at a corresponding common conductor junction such that the common conductor forms a thermocouple pair with each of the plurality of conductors.

15 Claims, 7 Drawing Sheets

(56) References Cited

U.S. PATENT DOCUMENTS

| | | |
|---|---|---|
| 2003/0135971 A1* | 7/2003 | Liberman .......... B01D 67/0041 29/419.1 |
| 2008/0161788 A1 | 7/2008 | Dando et al. |
| 2013/0123775 A1 | 5/2013 | Grunewald et al. |
| 2015/0157381 A1 | 6/2015 | Ashton et al. |
| 2015/0342671 A1 | 12/2015 | Govari et al. |

FOREIGN PATENT DOCUMENTS

| | | |
|---|---|---|
| WO | 1999056645 A2 | 11/1999 |
| WO | 2015/164280 A1 | 10/2015 |

* cited by examiner

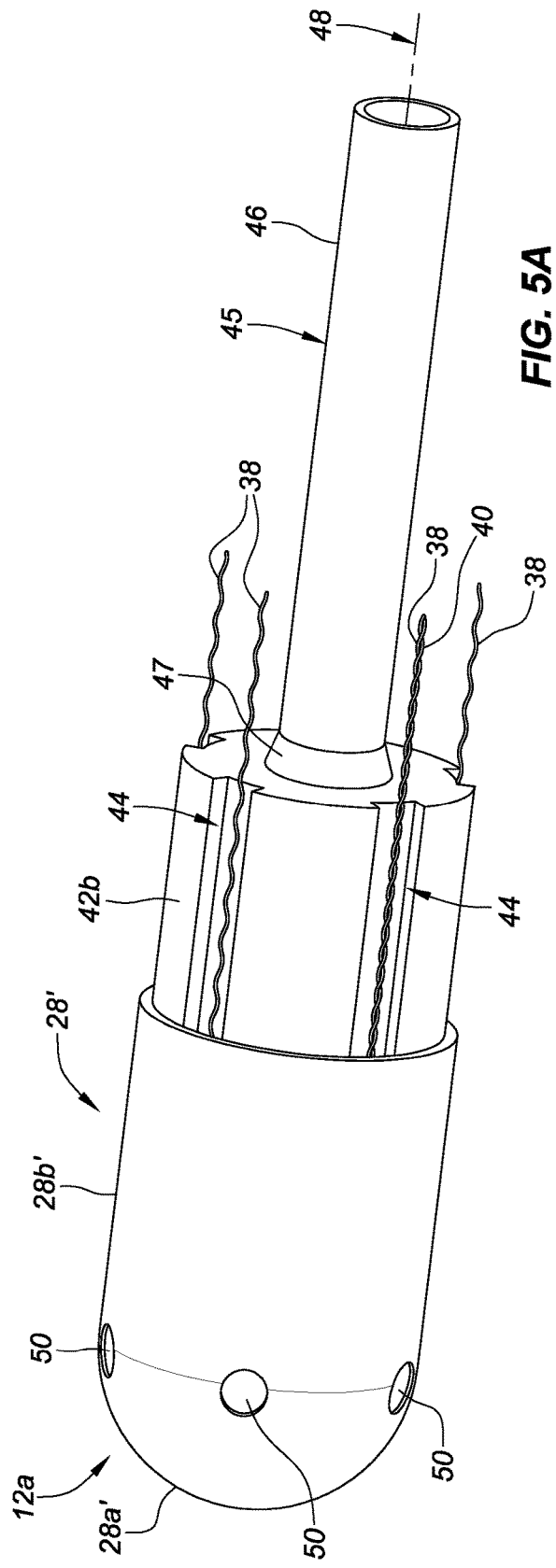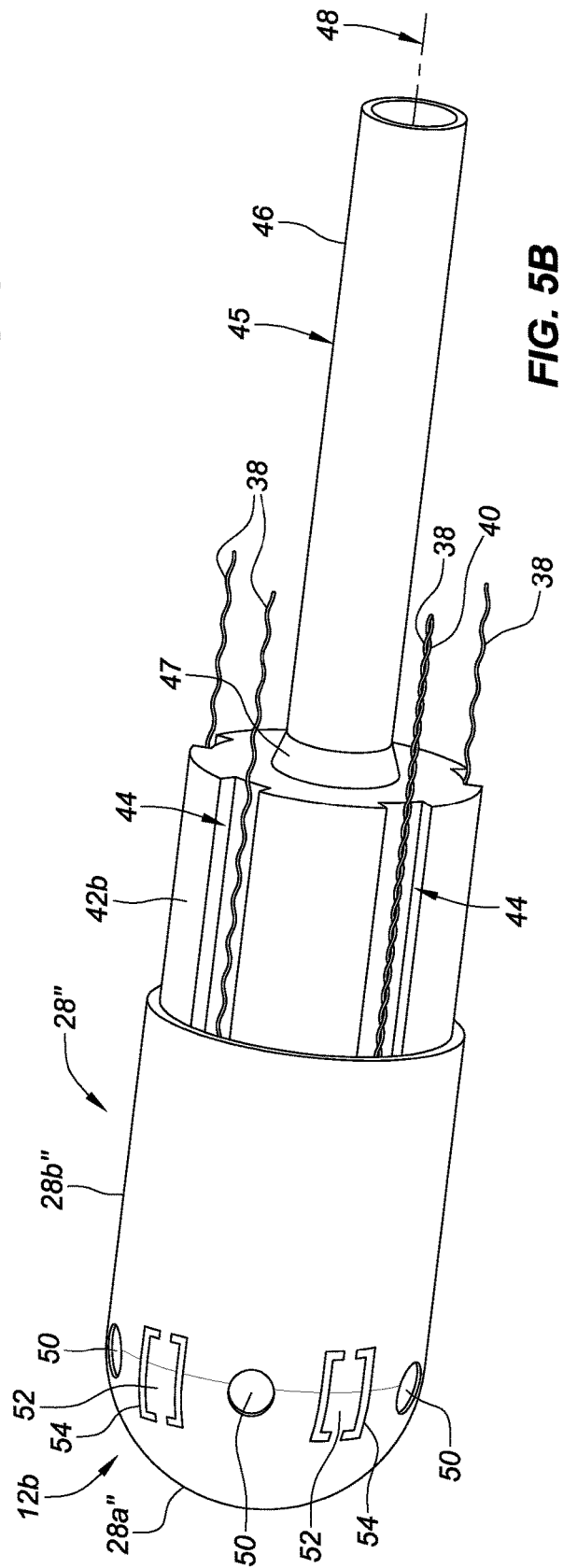

MULTIPLE THERMOCOUPLE ASSEMBLY WITH REDUCED WIRE COUNT

CROSS-REFERENCE TO RELATED APPLICATIONS

This application claims priority to U.S. provisional patent application No. 62/311,284 (the '284 application) titled "MULTIPLE THERMOCOUPLE ASSEMBLY WITH REDUCED WIRE COUNT," filed on 21 Mar. 2016. The '284 application is hereby incorporated by reference as though fully set forth herein.

BACKGROUND a. Field

The present disclosure generally relates to multiple thermocouples sharing a common wire.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include, for example, radio frequency (RF) ablation, cryoablation, laser ablation, chemical ablation, high-intensity focused ultrasound-based ablation, or microwave ablation. An electrophysiology catheter imparts ablative energy to cardiac tissue to create one or more lesions in the cardiac tissue and oftentimes, a contiguous, and transmural lesion. This lesion disrupts undesirable cardiac activation pathways and thereby limits, corrals, or prevents errant conduction signals that can form or sustain arrhythmias.

The foregoing discussion is intended only to illustrate the present field and should not be taken as a disavowal of claim scope.

BRIEF SUMMARY

In an embodiment, an elongate medical device comprising an assembly of multiple temperature sensors comprises a first metal material comprising a plurality of junctions; a plurality of conductors comprising a second metal material, each conductor connected to the first metal material at one of the plurality of junctions; and a common conductor that is physically paired with at least one of the plurality of conductors at a corresponding common conductor junction such that the common conductor forms a thermocouple pair with each of the plurality of conductors.

In another embodiment, an elongate medical device comprises a first metal material forming an ablation tip; a plurality of conductors comprising a second metal material, each conductor connected to the ablation catheter tip at one of a plurality of junctions; and a common conductor comprising a third metal material, wherein the common conductor forms a thermocouple pair with each of the plurality of conductors, and wherein the common conductor is physically paired with at least one of the plurality of conductors at a corresponding common conductor junction; and wherein a the junctions are configured such that a comparison of a voltage measured at each junction to a voltage measured at the common conductor junction is indicative of a corresponding temperature at each junction an assembly of multiple temperature sensors comprises a first metal material formed into a sheet or ring comprising a plurality of tabs; a plurality of wires comprising a second metal material, each wire connected to the sheet or ring at one of a plurality of junctions, each junction located on one of the plurality of tabs; and a common wire comprising a third metal material, wherein the common wire forms a thermocouple pair with each of the plurality of wires, and wherein the common wire is physically paired with at least one of the plurality of wires at a corresponding common wire junction; and wherein a comparison of a voltage measured at each junction to a voltage measured at the common wire junction is used to determine a corresponding temperature at each junction.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 5A is a proximal isometric view depicting an embodiment of the distal portion of an irrigated ablation catheter, in accordance with the present disclosure.

FIG. 5B is a proximal isometric view depicting another embodiment of the distal portion of an irrigated ablation catheter, in accordance with the present disclosure.

DETAILED DESCRIPTION

It can be desirable to monitor and/or control the temperature of an ablation catheter tip. It is important to accurately measure and maintain this temperature within a target range, high enough to create transmural lesions, but not so high as to result in steam pops or excessive tissue damage. RF ablation catheters can be configured to provide temperature feedback during RF ablation via a thermal sensor such as a thermocouple. Typically, the temperature reading provided by a single thermocouple cannot accurately represent the temperature of the tip/tissue interface. One reason is because a portion of the tip that is in direct contact with the targeted tissue can have a higher temperature than the rest of the tip that is being cooled by blood flow. The orientation of the RF ablation catheter can affect the position of the thermocouple, and accordingly, can affect the temperature reading provided by the thermocouple. If the thermocouple is in contact with the targeted tissue, the thermocouple can provide a certain temperature reading generally corresponding to the temperature of the targeted tissue. If the thermocouple is not in contact with the targeted tissue, the cooling effect of blood flow will prevent the thermocouple from ever approaching the actual temperature of the targeted tissue. In an effort to overcome the effect that the orientation of the catheter can have on temperature sensing, multiple thermocouples positioned at different locations in the tip can be used. For example and without limitation, the highest measured temperature can be used to represent the tip/tissue interface temperature.

It can also be desirable to reduce the number of wires required to provide multiple thermocouples at the tip of an ablation catheter, so as to provide more space for other catheter components (e.g., other types of sensors, such as position sensors or force sensors, for example) and to provide for easier assembly. The embodiments described herein can provide one or more of the aforementioned benefits.

Figure 1:
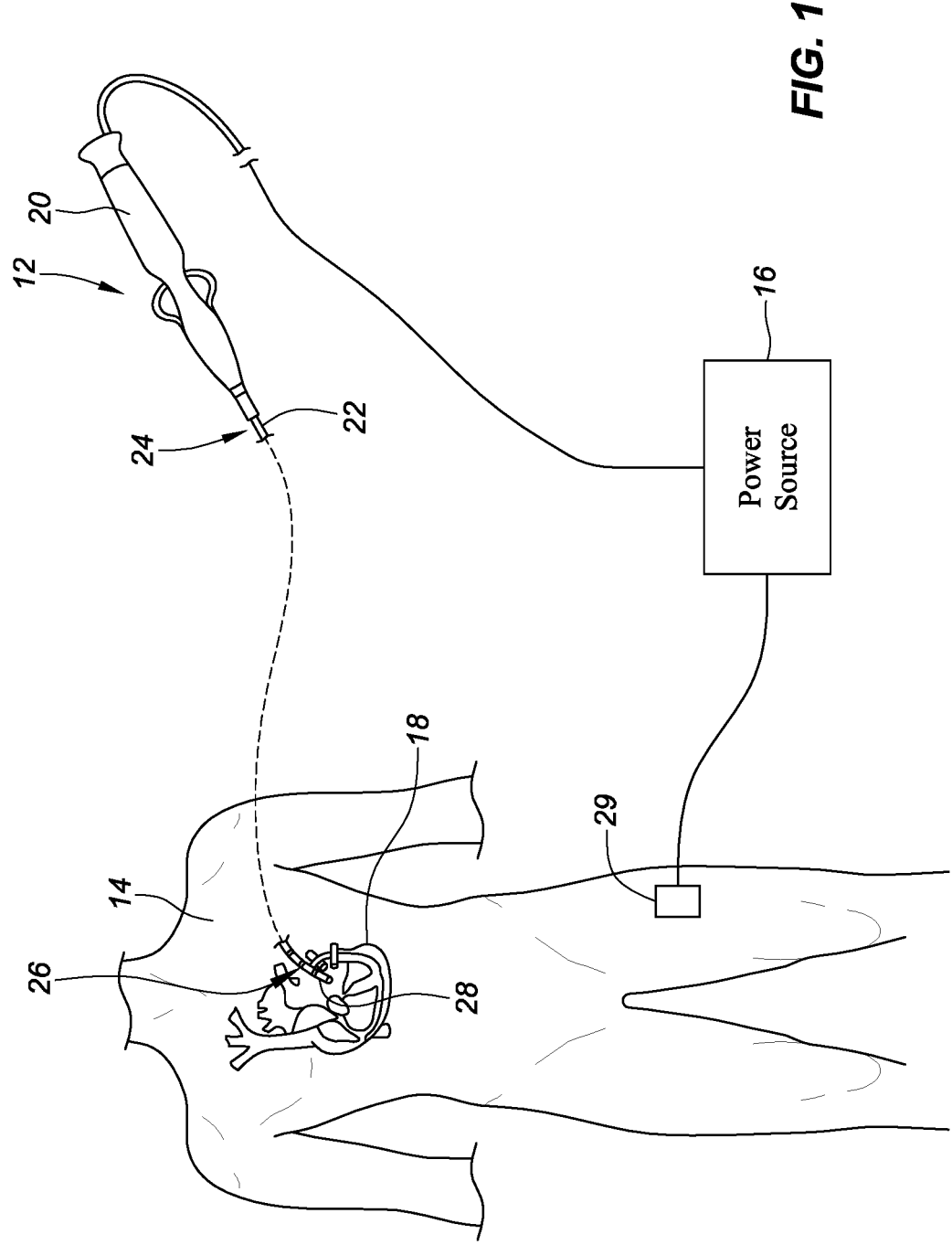
FIG. 1 is a schematic view depicting an ablation catheter in use in a patient and connected to a power source, in accordance with the present disclosure.

FIG. 1 is a schematic view depicting an ablation catheter 12 in use in a patient's body 14 and connected to a power source 16 (e.g., an RF ablation generator) according to the present disclosure. The ablation catheter 12 can be configured to be inserted into a the patient's heart 18. The ablation catheter 12 may include a handle 20 and a shaft 22 having a proximal end portion 24, a distal end portion 26, and a tip portion 28 disposed at the distal end portion 26 of the shaft 22. The ablation catheter 12 may further include other conventional components such as, for example and without limitation, a temperature sensor, a position sensor, additional sensors or electrodes, and corresponding conductors or leads. The tip portion 28 may include ablation elements (e.g., ablation tip electrodes for delivering RF ablative energy). A patch electrode 29 may function as an RF indifferent/dispersive return for an RF ablation signal.

The shaft 22 can be an elongate, tubular, flexible member configured for movement within the body 14. The tip portion 28 of the shaft 22 supports, for example and without limitation, sensors and/or electrodes mounted thereon, such as, for example, a temperature sensor assembly, which may include an assembly of temperature sensors and associated electronics, as described in detail below. The shaft 22 may also permit transport, delivery, and/or removal of fluids (including irrigation fluids, cryogenic ablation fluids, and bodily fluids), medicines, and/or surgical tools or instruments.

Figure 2:
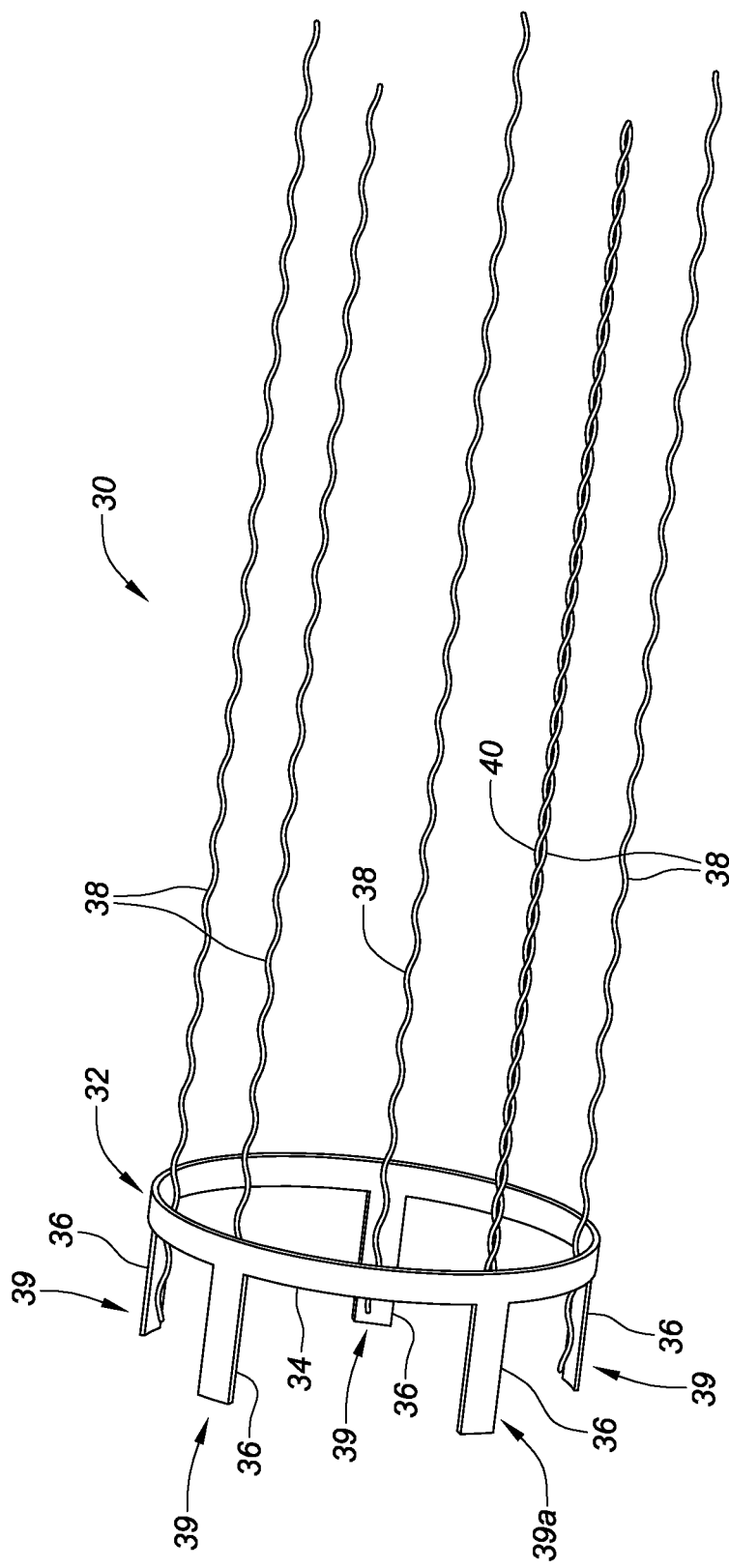
FIG. 2 is a proximal isometric view depicting an assembly of multiple temperature sensors configured to be inserted into a tip portion of an ablation catheter, in accordance with the present disclosure.

Referring to FIG. 2, an assembly of multiple temperature sensors 30 can be configured to be inserted into the tip portion 28 of the ablation catheter 12 (shown in FIG. 1). The assembly of multiple temperature sensors 30 can comprise a ring assembly 32, including a ring 34 and, optionally, a plurality of tabs 36 radially disposed symmetrically about the central axis of the ring 34 (not shown) and extending distally from the ring 34. In some embodiments, the plurality of tabs 36 can extend proximally from the ring 34. In other embodiments, at least one of the plurality of tabs 36 can extend distally from the ring 34 while at least one of the plurality of tabs 36 extends proximally from the ring 34. The ring assembly 32 can comprise a first metal material, such as constantan, which can be initially stamped from a sheet and then formed into a ring.

A plurality of conductors (for example, but not limited to, wires or conductive traces on flexible circuits or catheter components), referred to herein as a plurality of wires 38, comprising a second metal material, such as copper, can extend from the ring assembly 32. Although five wires 38 are depicted in FIG. 2, any number of wires can be used. Each of the plurality of wires 38 can be connected (e.g., soldered or welded) to the ring assembly 32 at one of a plurality of junctions 39, which can be located on one of the plurality of tabs 36, as shown. In another embodiment, the first metal material forming the ring assembly 32 can be copper and the second metal material forming the plurality of wires 38 can be constantan.

Finally, the assembly of multiple temperature sensors 30 can include a single common wire 40 formed from the first metal material (i.e., the same metal material as that forming the ring 34) and physically paired with (e.g., twisted or intertwined with) at least one of the plurality of wires 38. The common wire 40 can be joined to the ring assembly 32 at one of the plurality of junctions 39 located on one of the plurality of tabs 36. The junction at which the common wire 40 is joined to the ring assembly 32 is referred to as common wire junction 39a, as shown.

The above described structure of the assembly of multiple temperature sensors 30 allows the common wire 40 to form a thermocouple pair with each of the plurality of wires 38. A voltage measurement can be taken at each junction 39, as well as at the common wire junction 39a. By comparing the voltage at each junction 39 to the voltage at common wire junction 39a, the corresponding temperature at each junction 39 can be determined, as further described below. In an embodiment, the voltage can be measured at the distal end of each tab 36, thereby providing a long thermal path between junctions 39, 39a. This ensures that the temperature taken at one junction is essentially independent of the temperature taken at other junctions and that there is minimal thermal conduction between junctions.

Figure 3A:
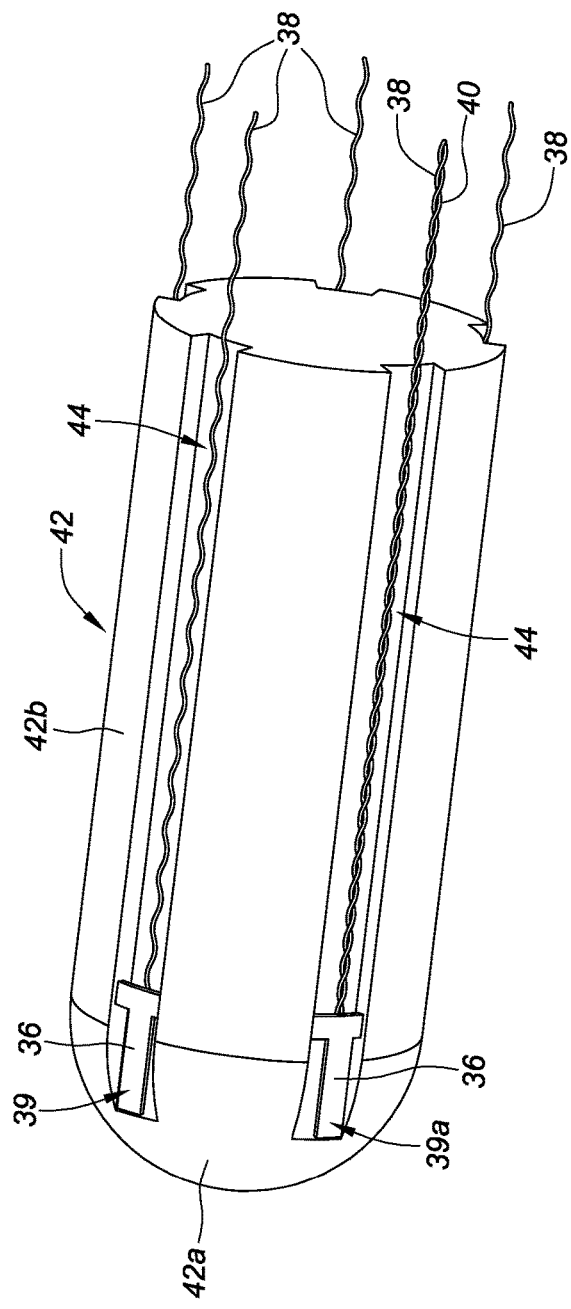
FIG. 3A is a proximal isometric view depicting the assembly of multiple temperature sensors of FIG. 2 together with a plastic insert configured to be inserted into the tip portion of an ablation catheter, in accordance with the present disclosure.

Turning now to FIG. 3A, the assembly of multiple temperature sensors 30 can be seen assembled together with a plastic insert 42, which can be configured to be inserted into the tip portion 28 of the catheter 12. The plastic insert 42 comprises a domed distal end 42a connected to a cylindrical body 42b. The plastic insert 42 can include a plurality of grooves 44, radially disposed and running longitudinally along the outer surface of the cylindrical body 42b and a portion of the domed distal end 42a. Each of the plurality of grooves 44 can be configured to surround at least one of the plurality of wires 38, including the wire/common wire pair 38/40. The plastic insert 42 can be designed to provide structural support, as well as high thermal isolation between each of the plurality of junctions 39, 39a.

Figure 3B:
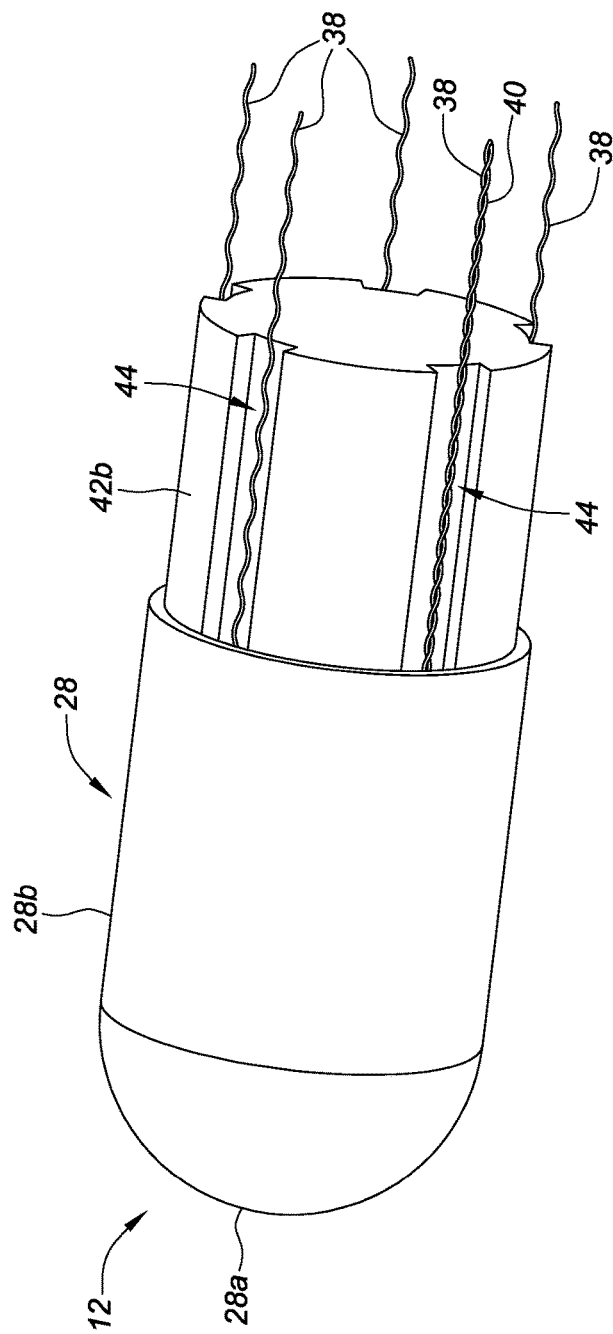
FIG. 3B is a proximal isometric view depicting the assembly of multiple temperature sensors of FIG. 3A together with an electrode shell covering the distal portion of the temperature sensor assembly, in accordance with the present disclosure.

FIG. 3B is similar to FIG. 3A, but shows the tip portion 28 of the catheter 12 partially covering the plastic insert 42 and multiple temperature sensor assembly 30. Similar to the plastic insert 42, the tip portion 28 can include a domed distal end 28a and a cylindrical body 28b. The tip portion 28 can comprise a thin-walled metal shell, such as platinum, gold, or a platinum-iridium alloy, for example. A thin dielectric layer (not shown), such as Kapton™ (polyimide) tape, can be placed between the ring assembly 32 and the tip portion 28 in order to provide electrical isolation (but not thermal isolation) and prevent averaging of the sensed thermocouple voltage at each junction 39, 39a.

Figure 4:
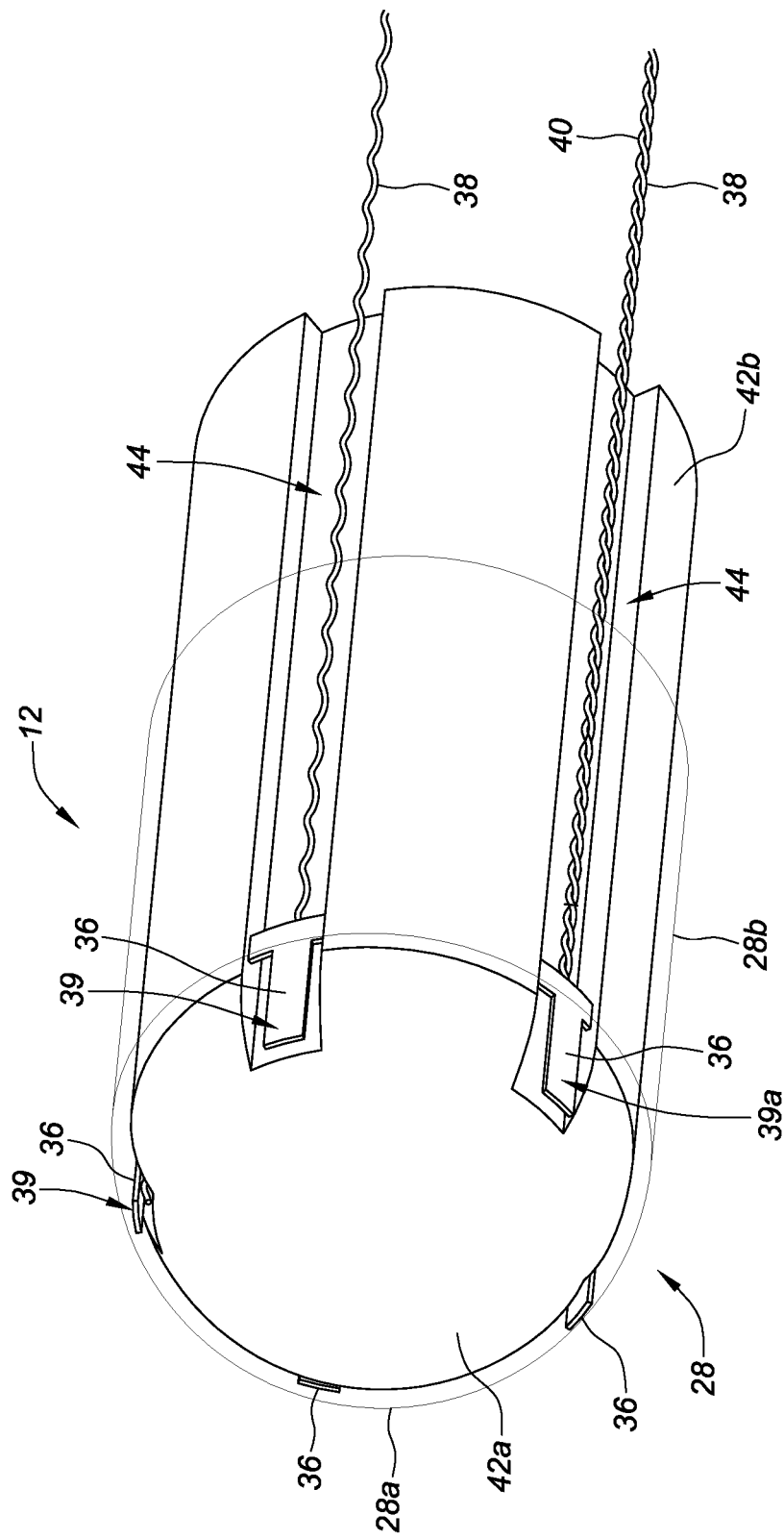
FIG. 4 is a distal isometric view depicting the assembly of multiple temperature sensors shown in FIG. 3B, in accordance with the present disclosure.

Turning now to FIG. 4, a distal isometric view of the assembly of multiple temperature sensors of FIG. 3B is shown. Here, the tip portion 28 is illustrated as translucent in order to illustrate the interference fit between the tabs 36 and the tip portion 28. A tight fit between the tabs and the tip portion allows for good thermal conduction, and, in turn, accurate temperature measurement at the plurality of junctions 39, 39a.

While the catheter 12 has been depicted as a non-irrigated catheter the above figures, other embodiments can include irrigated catheters. FIGS. 5A and 5B depict examples of irrigated catheters 12a and 12b, respectively, in accordance with the present disclosure. An irrigation tube assembly 45 is positioned along the central longitudinal axis 48 of the catheters 12a and 12b. The irrigation tube assembly comprises, in this embodiment, a central irrigation tube 46 and an optional seating sleeve 47. The central irrigation tube 46 can be constructed from a polymer, such as polyimide. The optional seating sleeve 47 can include a cylindrical portion and a frustoconical boss. The seating sleeve 47 may be positioned at a desired longitudinal location along the outer surface of the central irrigation tube 46 and then may be fixed in place (for example, by an adhesive or sonic welding or via some other technique). The irrigation tube assembly 45 would then be mounted in the plastic insert cylindrical body 42b by, for example, adhesive. If the optional seating sleeve 47 is not included (e.g., to simplify tip construction and manufacturing), the central irrigation tube 46 could be adhered directly to the plastic insert cylindrical body 42b. For additional details regarding such an irrigated catheter design, see U.S. Provisional Patent Application No. 62/198,114, filed on 28 Jul. 2015, titled "Methods and devices for delivering pulsed RF energy during catheter ablation," incorporated by reference in its entirety as though fully set forth herein.

FIGS. 5A and 5B also depict a plurality of irrigation holes 50, radially disposed symmetrically about the domed distal ends 28a' and 28a" of the tip portions 28' and 28", respectively. The irrigation holes 50 are located mid-way between the junctions 39, 39a (shown in FIGS. 2, 3A, and 4). Although five irrigation holes 50 (two visible in FIGS. 5A and 5B) are depicted, more or fewer holes may be used, and the size of the holes may be larger, or smaller, or a mix of larger and smaller holes. The plastic insert 42 can include a plurality of lateral irrigation holes (not shown) that are sized and arranged to align with complimentary irrigation holes 50 through the tip portions 28' and 28".

FIG. 5B shows another embodiment in which one or more temperature-sensing islands resides partially on the domed distal end 28a" and partially on the cylindrical body 28b" of tip portion 28". Each temperature-sensing island 52 is positioned such that it overlies a junction 39, 39a (see, e.g., FIGS. 3A and 4). The temperature-sensing islands 52 are outlined or circumscribed by a strip of insulative material 54 placed to reduce or eliminate any potential influence from irrigant flowing through the nearby irrigation holes 50 in the tip portion 28". In particular, if the cooled irrigant flowing through an irrigation hole 50 meaningfully reduces the temperature of the domed distal end 28a" of the tip portion 28" surrounding the irrigation hole 50, that lower temperature would not readily be transmitted to a temperature sensor, such as the thermocouples at junctions 39, 39a, mounted within the tip portion 28" below the temperature-sensing island 52.

Returning now to FIG. 2, determination of the temperature at each junction 39, 39a based on thermocouple voltage will be further discussed. Thermocouple voltage measurements can be taken at each junction 39, 39a using conventional means known in the art, provided that the instrumentation used to sense the voltage is very high impedance and there is insignificant current flowing through each thermocouple (to prevent averaging of the voltages sensed at each junction). The voltages sensed at each junction 39, 39a will correspond to the junction temperature in the manner predicted by traditional thermocouple coefficients (Seebeck coefficients. It is desirable, however, to minimize thermal conduction between junctions 39, 39a, as discussed above. Thermal isolation minimizes the averaging effect that may otherwise occur when junctions are near each other, allowing for improved detection of hot spots created during the ablation procedure. As discussed above, measuring the voltage at the distal end of each narrow tab 36 provides a long thermal path between junctions 39, 39a, which, in turn, improves thermal isolation between junctions 39, 39a.

Additionally, the choice of material can assist in providing thermal isolation between junctions 39, 39a. As previously discussed, in one embodiment the ring assembly 32 and the common wire 40 comprise constantan, while the plurality of wires 38 comprise copper. This particular choice of materials can be advantageous because copper has a very low electrical resistance and corresponding low thermal impedance, resulting in high thermal conductivity. Constantan, on the other hand, has a much higher electrical resistance and higher thus higher thermal impedance, resulting in a low thermal conductivity. Therefore, heat applied to one tab 36 of a constantan ring assembly 32 will have much less effect on a neighboring tab 36 than if the ring assembly 32 was composed of copper. In addition, when choosing a material for the tip portion 28 of the catheter 12, platinum-iridium can be preferable to pure platinum or gold because platinum-iridium has a much lower thermal conductivity than pure metals, which would aid in thermally isolating junctions.

Using this combination of materials, a thin dielectric layer (discussed above with respect to FIG. 3B) may need to be placed between the constantan ring assembly 32 and the platinum-iridium tip portion 28 in order to provide electrical isolation and prevent averaging of the sensed thermocouple voltage at each junction 39, 39a. Use of such a dielectric layer can be disadvantageous, however, because dielectrics are usually poor thermal conductors, meaning there may be a slight temperature error from the external surface of the tip portion 28 directly above a thermocouple junction and the junction itself. To avoid any such temperature error, the dielectric layer can be eliminated in the embodiment described below.

Figure 6:
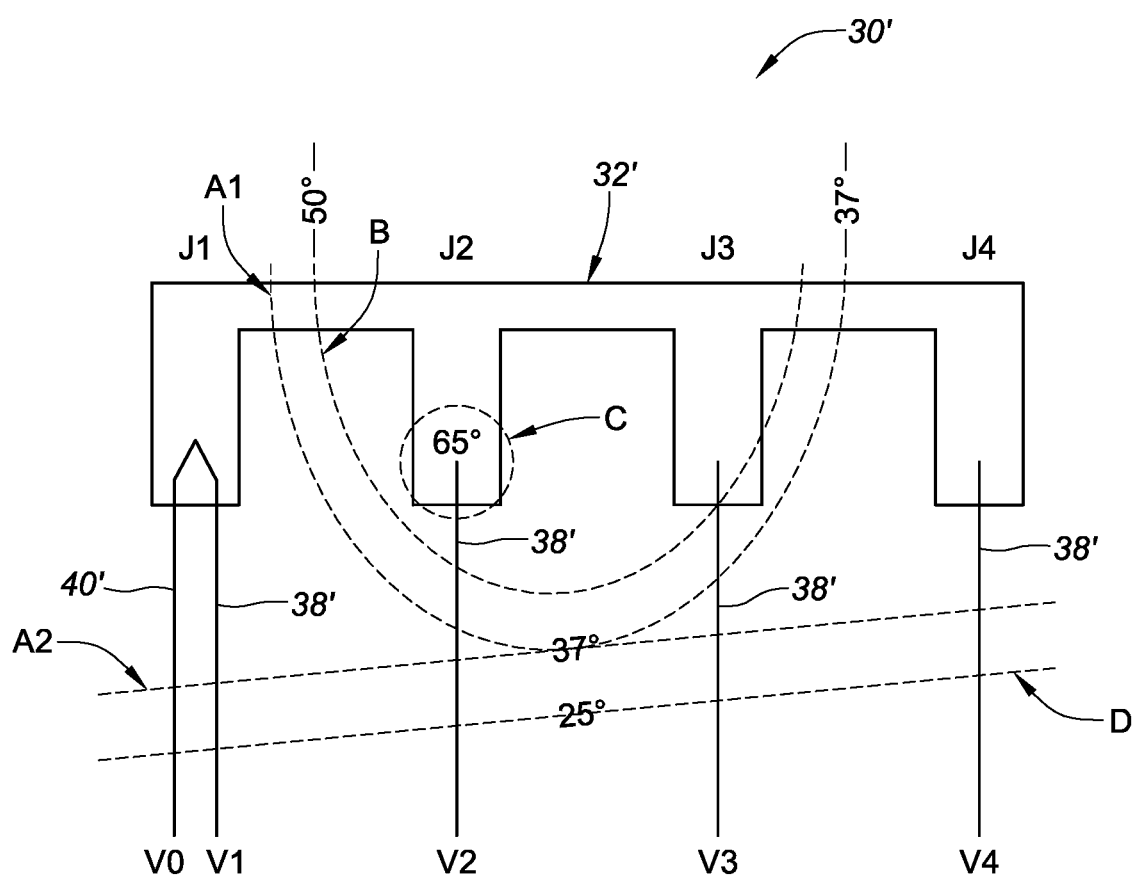
FIG. 6 is a schematic view of depicts an embodiment of a temperature sensor assembly, in accordance with the present disclosure.

FIG. 6 depicts an embodiment of a multiple temperature sensor assembly 30', in which a ring assembly 32' (shown here in sheet form with four thermocouples and four junctions J1-J4) comprises platinum-iridium, along with the tip portion 28 (shown in FIGS. 3B and 4). A common wire 40' can comprise copper, and a plurality of wires 38' can comprise constantan (although this may be reversed). In another embodiment, the common wire 40' can comprise platinum-iridium. In any case, the benefit of having both the ring assembly 32' and the tip portion 28 made of the same material (i.e., platinum-iridium) is that the ring assembly 32' can make direct contact with the inner surface of the tip portion 28, thereby allowing for the highest thermal conductivity at each junction J1-J4. No dielectric layer is needed between the ring assembly 32' and tip portion 28 is needed in this embodiment since both are made from the same metal. Nevertheless, because of the direct connection to the tip portion 28 and its ablation voltage, the thermocouple circuits/junctions must be electrically isolated from the earth ground.

An example of a theory of operation of the multiple temperature sensor assembly 30' will now be described with respect to FIG. 6. As shown by the dashed isothermal lines A1, A2, and B, and dashed circle C (signifying an isothermal island), the temperatures of the four thermocouples at each of the respective junctions J1-J4 are as follows:

$$T_{J1}=37° C., T_{J2}=65° C., T_{J3}=50° C., T_{J4}=37° C.$$

In addition, an independently known cold junction $T_{CJ}=25°$ C., as shown by dashed isothermal line D.

For illustration purposes, Seebeck coefficients are assumed to be known constants as follows (these are only approximate values for illustration purposes, as exact values may vary with temperature but are reasonably constant over the temperature ranges encountered during ablation).

$$\text{Constantan}=S_{cn}=-35 \text{ uV}/° C.$$

$$\text{Copper}=S_{cu}=+7 \text{ uV}/° C.$$

$$\text{Platinum-Iridium (90/10)}=S_{PtIr}=+12 \text{ uV}/° C.$$

It is assumed that V0 is the voltage measured between the common copper wire 40' and the sensing circuit reference, and that V0 is zero volts by definition (at the cold junction).

The voltage V1 at junction J1, relative to V0, may be determined by summing around the loop. For illustration, the individual voltage gradients are summed. Thus, starting from the common copper wire 40', each gradient term is added:

$$V1=[S_{Cu}*(T_{CJ}-T_{J1})]+[S_{Cn}*(T_{J1}-T_{CJ})]$$

$$V1=[7 \text{ uV}*(25-37)]+[-35 \text{ uV}*(37-25)]$$

$$V1=[-84 \text{ uV}]+[-420 \text{ uV}]=-504 \text{ uV}$$

In practice, the voltage V1 can be measured and used to solve for the junction temperature $T_{J1}$, since cold junction $T_{CJ}$ and the Seebeck constants are known. Thus:

$$T_{J1}=T_{CJ}+(504 \text{ uV}/42 \text{ uV})=25+12=37° C. \text{ (sign adjusted)}$$

The voltage V2 at junction J2 can be determined in a similar way, however, multiple gradients must be considered. Starting from the common copper wire 40' as before, the first gradient is from 25° C. to 37° C. and the voltage is [7 uV*(25−37)]. The Pt—Ir material of the ring assembly 32' connects J1 to J2 with a temperature gradient of 37° C. to 65° C. for a voltage of [12 uV*(37−65)]. The constantan material of wire 38' connects J2 to the voltage measuring point V2 at the cold junction temperature of 25° C. for a voltage of [−35 uV*(65−25)]. Therefore:

$$V2=[S_{Cu}*(T_{CJ}-T_{J1})]+[S_{PtIr}*(T_{J1}-T_{J2})]+[Scn*(T_{J2}-T_{CJ})]$$

$$V2=[7 \text{ uV}*(25-37)]+[12 \text{ uV}*(37-65)]+[-35 \text{ uV}*(65-25)]$$

$$V2=-84 \text{ uV}-336 \text{ uV}-1400 \text{ uV}=-1820 \text{ uV}$$

In practice, V2 can be measured and junction temperatures can be calculated as before. However, calculating the junction temperature $T_{J2}$ requires knowledge of not only $T_{CJ}$, but also $T_{J1}$ per the above equation. Because $T_{J1}$ has already been calculated, $T_{J2}$ can be calculated by simple rearranging and collecting of terms. For example:

$$V2=-1820 \text{ uV (by measurement)}$$

$$V2=[S_{Cu}*(T_{CJ}-T_{J1})]+[S_{PtIr}*(T_{J1}-T_{J2})]+[S_{cn}*(T_{J2}-T_{CJ})]$$

$$V2=[S_{Cu}*(T_{CJ}-T_{J1})]+[S_{PtIr}*T_{J1}]-[S_{PtIr}*T_{J2}]+[S_{cn}*T_{J2}]-[S_{cn}*T_{CJ}]$$

$$[S_{PtIr}*T_{J2}]-[S_{cn}*T_{J2}]=[S_{Cu}*(T_{CJ}-T_{J1})]+[S_{PtIr}*T_{J1}]-[S_{cn}*T_{CJ}]-V2$$

$$[(S_{PtIr}-S_{cn})*T_{J2}]=[S_{Cu}*(T_{CJ}-T_{J1})]+[S_{PtIr}*T_{J1}]-[S_{cn}*T_{CJ}]-V2$$

$$T_{J2}=([S_{Cu}*(T_{CJ}-T_{J1})]+[S_{PtIr}*T_{J1}]-[S_{cn}*T_{CJ}]-V2)/(S_{PtIr}-S_{cn})$$

$$T_{J2}=([7 \text{ uV}*(25-37)]+[12 \text{ uV}*(37)]-[-35 \text{ uV}*25]+1820 \text{ uV})/(12 \text{ uV}+35 \text{ uV})$$

$$T_{J2}=(-84 \text{ uV}+444 \text{ uV}+875 \text{ uV}+1820 \text{ uV})/(12 \text{ uV}+35 \text{ uV})$$

$$T_{J2}=65° C.$$

Temperature $T_{J3}$ is found in a similar way. The hot spot at J2 does not interfere with the reading at J3 due to rule of intermediate temperatures. Thus, only the temperature gradient of J1 to J3 needs to be used.

Temperature $T_{J4}$ is found a similar way. In this example, where $T_{J4}=T_{J1}$, it will be found there is no voltage gradient across the platinum-iridium ring assembly 32' between J4 and J1. The resulting voltage is identical to a T-type thermocouple at this temperature due to the rule of intermediate metals (that is, when an intermediate metal has the same temperature at both ends, it makes no contribution to the voltage). However, without knowing a priori that this is the case, the calculation must still be performed.

Thus it is useful to recognize that there is no single Seebeck coefficient that can be applied to all the thermocouple junctions except for the first junction (the first being type T in this case). However, it is a straightforward calculation to apportion the coefficients and calculate the temperature for every thermocouple junction.

Figure 7A:
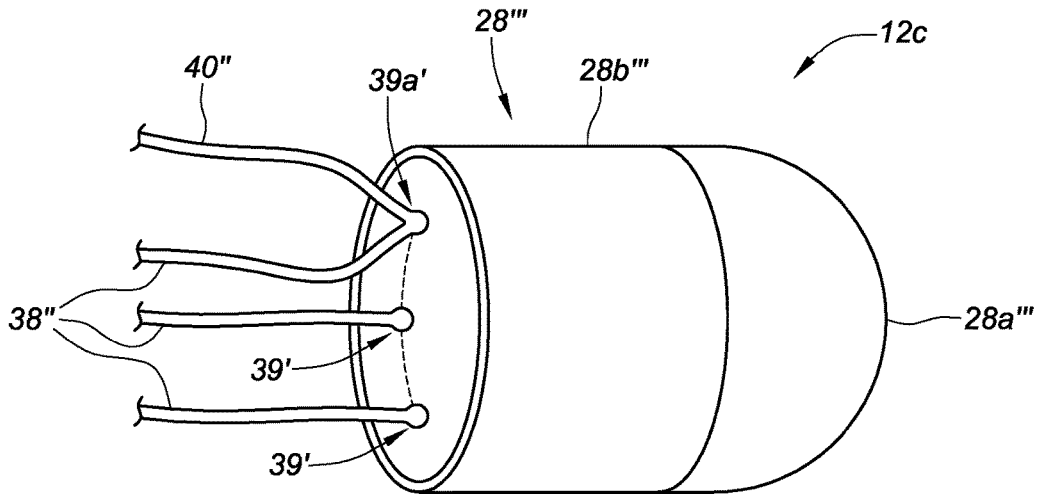
FIG. 7A is a proximal isometric view depicting an embodiment of a temperature sensor assembly, in accordance with the present disclosure.
Figure 7B:
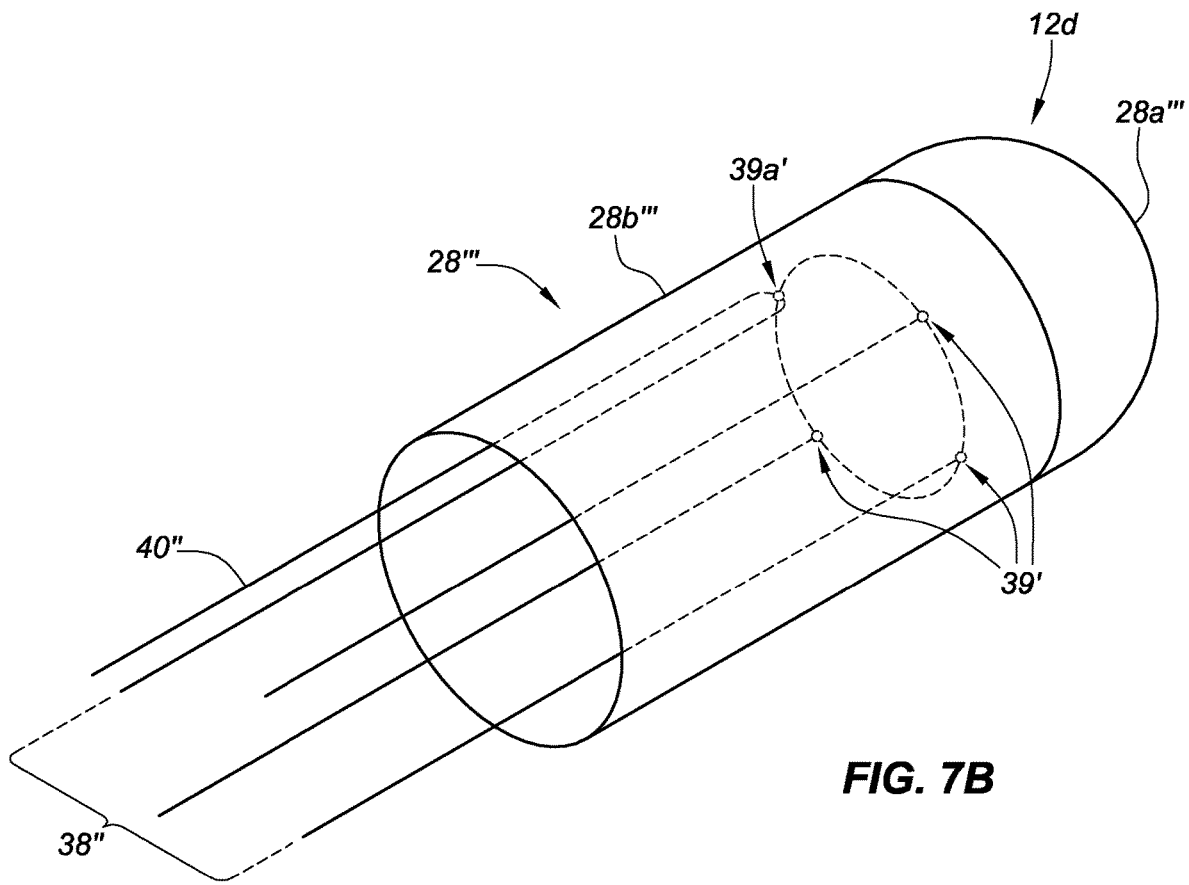
FIG. 7B is a proximal isometric view depicting another embodiment of a temperature sensor assembly, in accordance with the present disclosure.

FIGS. 7A and 7B depict ablation catheters 12c and 12d, respectively, with embodiments of multiple temperature sensor assemblies. In these embodiments, there is no ring assembly; instead, junctions 39', 39a' (similar to junctions 39, 39a shown and described with respect to FIGS. 2, 3A, and 4) are directly connected, physically and electrically, to the inner surface of the tip portion 28''' of the catheters 12c and 12d. The junctions 39', 39a' can be connected to the cylindrical body 28b''' or to the domed distal end 28a''' of the tip portion 28''', or to a combination of both. As shown in FIG. 7B, the junctions 39', 39a' can be located radially 90 degrees apart inside the tip portion 28'''. In other embodiments, the junctions can be located at different and/or multiple radial angles.

The temperatures at junctions 39', 39a' can be calculated similarly to those of junctions J1-J4 in FIG. 6, as described above. To minimize thermal conduction between junctions, for the previously described reasons, the tip portion 28''' can be preferably constructed using very thin walls. This can ensure that the temperature taken at one junction is essentially independent of the temperatures taken at other junctions. Thermal isolation can be further enhanced by using platinum-iridium for the tip portion 28''' instead of more thermally conductive materials, such as pure platinum or gold. It should be noted that temperature calculations with alternate materials can be conducted in the same manner described above, provided the appropriate Seebeck coefficient for the substituted material is used in the calculations.

Although several embodiments have been described above with a certain degree of particularity, those skilled in the art could make numerous alterations to the disclosed embodiments without departing from the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An elongate medical device comprising an assembly of multiple temperature sensors, the assembly comprising:
   a first metal material comprising a plurality of junctions;
   a plurality of conductors comprising a second metal material, each of the plurality of conductors connected to the first metal material at one of the plurality of junctions; and
   a single common conductor that is physically paired with at least one of the plurality of conductors at a corresponding single common conductor junction such that the single common conductor forms a thermocouple pair with each of the plurality of conductors;
   wherein the first metal material has a higher thermal resistance than the second metal material; and
   wherein a distal tip portion of the elongate medical device comprises an outer shell comprising at least one of platinum, platinum-iridium, or gold.

2. The elongate medical device of claim 1, wherein the plurality of junctions is configured such that a comparison of a voltage measured at each of the plurality of junctions to a voltage measured at the single common conductor junction is indicative of a corresponding temperature at each of the plurality of junctions.

3. The elongate medical device of claim 1, wherein the first metal material comprises constantan and the second metal material comprises copper.

4. The elongate medical device of claim 1, wherein each of the plurality of junctions is in thermal contact with a tip of the elongate medical device.

5. The elongate medical device of claim 1, wherein the distal tip portion of the elongate medical device is configured for use with an irrigated ablation catheter.

6. The elongate medical device of claim 1, wherein each of the plurality of junctions is thermally isolated from other junctions.

7. The elongate medical device of claim 1, wherein each of the plurality of junctions is located at a distal end of a tab.

8. The elongate medical device of claim 1, wherein the first metal material is formed into a sheet or ring, and wherein the sheet or ring is electrically insulated.

9. The elongate medical device of claim 1, wherein the single common conductor comprises the first metal material.

10. The elongate medical device of claim 1, wherein each of the plurality of conductors comprises a wire or a conductive trace.

11. The elongate medical device of claim 1, wherein the single common conductor comprises a third metal material.

12. The elongate medical device of claim 11, wherein the first metal material comprises at least one of platinum or platinum-iridium, the second metal comprises constantan, and the third metal comprises copper.

13. The elongate medical device of claim 11, wherein the first metal material comprises at least one of platinum or platinum-iridium, the second metal comprises coper, and the third metal comprises constantan.

14. The elongate medical device of claim 11, wherein each of the plurality of junctions is in direct electrical contact with a tip of the elongate medical device.

15. The elongate medical device of claim 11, wherein each of the plurality of junctions is electrically isolated from earth ground.

* * * * *